United States Patent [19]

Lasure et al.

[11] Patent Number: 5,025,910
[45] Date of Patent: Jun. 25, 1991

[54] ROTARY PAD TURNER

[75] Inventors: Randal D. Lasure, Wellington; Werner Schweizer; Ari Venetjoki, both of Boynton Beach, all of Fla.

[73] Assignee: Curt G. Joa, Inc., Sheboygan Falls, Wis.

[21] Appl. No.: 474,537

[22] Filed: Feb. 2, 1990

[51] Int. Cl.⁵ .............................................. B65G 17/32
[52] U.S. Cl. .................................................... 198/377
[58] Field of Search ............... 198/379, 377, 441, 450; 271/194, 196

[56] References Cited

U.S. PATENT DOCUMENTS

| | | | |
|---|---|---|---|
| 4,523,671 | 6/1985 | Campbell | 198/441 X |
| 4,574,022 | 3/1986 | Johnson et al. | 198/377 X |
| 4,582,201 | 4/1986 | Taniguchi et al. | 198/377 X |
| 4,738,348 | 4/1988 | Sillner | 198/377 X |

*Primary Examiner*—Joseph E. Valenza
*Assistant Examiner*—Keith L. Dixon
*Attorney, Agent, or Firm*—Fuller, Ryan & Hohenfeldt

[57] ABSTRACT

Apparatus for turning pads through an angle of 90° about an axis perpendicular to their plane as they are orbited with a drum from a pad pickup station to a pad transfer station. The drum has a plurality of circumferentially spaced apart supports inside of it. A hollow shaft extends radially out of each support and has a vacuum pickup shoe on it. A pinion is fastened concentrically to the hollow shaft and a gear in the support turns the pinion. A cam follower engages in the groove of a stationary circular cam. As the drum rotates the cam follower arrives in a part of the cam groove which turns the gear and results in the hollow shaft and the vacuum shoe being turned through an angle of 90° as the shoe is orbited from the pad pickup station to the pad transfer station. Flexible tubes connect ports in the base of the drum to the hollow vacuum shaft. The ports run over a curved groove in a stationary vacuum platen at times when vacuum must be applied to the shoe and run off of the groove and cut off the vacuum of the shoe at the pad transfer station where pads are transferred to a rotating vacuum drum.

6 Claims, 5 Drawing Sheets

ROTARY PAD TURNER

BACKGROUND OF THE INVENTION

The invention disclosed herein is a machine for rotating articles such as female sanitary pads as they advance along a production line. Oblong sanitary pads are the articles which will be used to demonstrate the structure and function of the new machine, but it should be understood that the machine can be used to turn other articles having any shape also.

Sanitary pads are oblong articles composed of a core of fluid absorbent material captured between a front sheet of fluid permeable material and a back sheet of fluid impermeable material. When the pads are discharged from the output of the pad fabricating machine to a conveyor, they are moving along a path that is coincident with or parallel to their long or longitudinal axis. This is not the proper orientation for transferring the pads to a folder or a stacker which groups them for packaging. The back sheet is rather stiff so the pads are folded before being packaged with the soft front sheet areas overlaying and with the stiffer back sheet on the outside. Folding oppositely would result in the stiffer back sheet bunching up or wrinkling which is undesirable.

Before stacks of pads are pushed into cartons or bags in a packaging machine, it is common practice to fold them to form two or three layers and encapsulate them in individual packages. This allows the user to remove one wrapped pad at a time from the carton and carry it in a purse, for instance, for use when occasion arises. Prefolding results in the pad being shortened and made more compact to make it easier to carry in a purse. Folding machines are so designed that it is necessary to convey the pads to the input of the machine while their long dimension is transverse to the direction in which they are moving on the conveyor to facilitate folding. The machine combination described herein rotates the pads 90° about an axis which is perpendicular to the center of the pad.

Two different kinds of pad turning machines are described in U.S. Pat. Nos. 4,619,357 and 4,751,997, respectively, which are assigned to the assignee of the present invention. The pad turning machine described herein is adapted for higher production rates than could be achieved with the machines described in the patents.

SUMMARY OF THE INVENTION

The new pad turner features high speed turning and transfer rates. An important feature of the new machine is that it is adapted for handling pads of different widths and lengths without making any mechanical changes or adjustments in the machine before switching from handling one pad size to another.

In general terms, the new pad turner comprises a rotor in the form of a drum which is closed at one end by a plate. The drum carries several, eight for instance, mechanisms which rotate radially extending axially bored or tubular shafts, associated with each of them, back and forth through a rotational angle of 90. A curved shoe is mounted to each of the shafts. The shoes have a plurality of perforations which allow a vacuum to be drawn on the curved faces of the shoes. At an angle or the drum rotation wherein pads are picked up at a pickup station by successive shoes, the pad is moving in the direction of its long axis and approaches a shoe with its long dimension or axis coextensive with the long dimension of the pickup shoe in the illustrated embodiment. After the pad is secured to the shoe under the influence of vacuum, the turning mechanism for that shoe begins to rotate the bored or hollow vacuum conducting shaft on which the shoe is mounted so as to begin orienting the shoe transversely to the direction in which the drum is rotating. The shoe and the pad thereon are fully rotated through an angle of 90° by the time the pad reaches the transfer or pad release station so the oblong pad continues to move thereafter in the direction of its short axis with its long axis transverse to the direction in which it is moving. Transfer of each pad is then made to a vacuum drum from the drum to a conveyor.

A more detailed description of a preferred embodiment of the invention will now be set forth in reference to the drawings.

DESCRIPTION OF A PREFERRED EMBODIMENT

Figure 8:
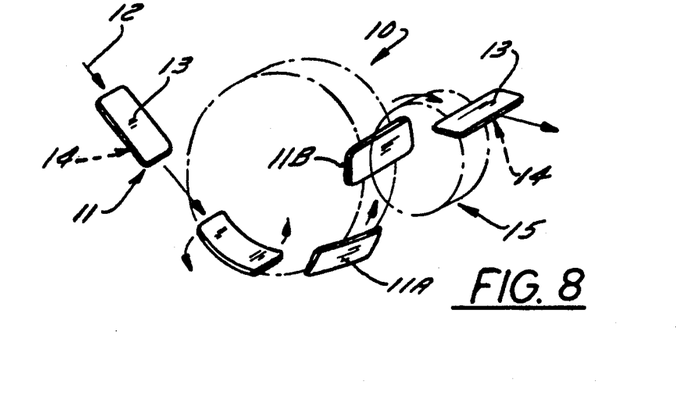
FIG. 8 is a diagram indicating the motions which each pad experiences in connection with being turned 90° from the line along which its long axis was initially traveling to moving in the direction of its shorter axis.

Attention is invited to the FIG. 8 diagram which shows the operating principles of the pad turning system. A rotor comprised of a drum is designated generally by the reference numeral 10. An incoming pad is indicated by the numeral 11. It is moving along a line coincident with one of its axes such as its long axis as indicated by the arrow marked 12. The top side 13 of the pad is faced with a porous non-woven sheet so it is permeable to fluids. The underside 14 of the pad is faced with a fluid impermeable sheet which makes the bottom side stiffer than the top side of the pad. One of the pads marked 11A is experiencing rotation about an axis that is perpendicular to the rotational axis of the rotor 10 and another pad marked 11B is fully rotated so that it is now being carried around on the rotor or drum in a direction aligned with the other of its axes, particularly the narrow or short axis of the pad. While the pads are being carried on the drum, they are being held by vacuum applied to the porous side of the pads and the stiffer non-porous face 14 is faced away from the drum. Pad 11B is in the position to be transferred from drum 10 to a vacuum drum which is generally designated by the numeral 15. After the transfer, the non-porous fluid impermeable face 14 of the pad has the vacuum applied to it by the drum 15 and the porous sheet or face 13 is facing upward.

Figure 9:
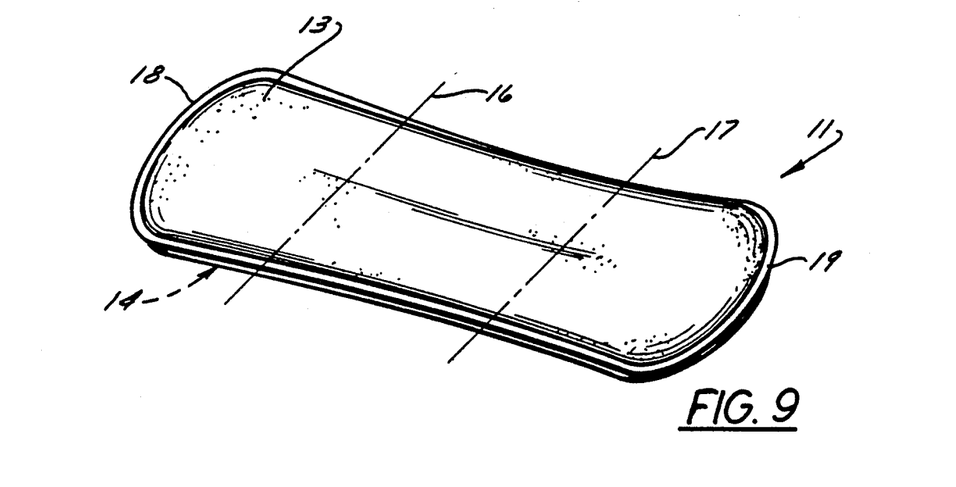
FIGS. 9 and 10 depict two kinds of sanitary pads which are typical of those which may be handled by the new turner.

A typical pad of one style is depicted in FIG. 9. The top side of the pad has the porous facing sheet 13 and the bottom side 14 has the fluid impervious sheet And, although the absorbent pad between the sheets is not visible, it is well known to be captured in between the facing sheets 13 and 14. Subsequent to the pads leaving the vacuum drum 15, they may be folded along the lines 16 and 17 in which case the end 18 of the pad would be folded clockwise and the other end 19 would be folded counterclockwise so that these ends would be adjacent each other and overlaying the central portion of the pad. In other words, the porous sheet is on the inside of the fold and the stiffer non-porous backing sheet 14 is on the outside of the fold and placed in tension rather than in compression which would occur if the pads were folded oppositely so that the stiffer backing sheet would be on the inside of the folds. The fold could be made on a center line which is not shown but would be centered between lines 16 and 17.

Figure 10:
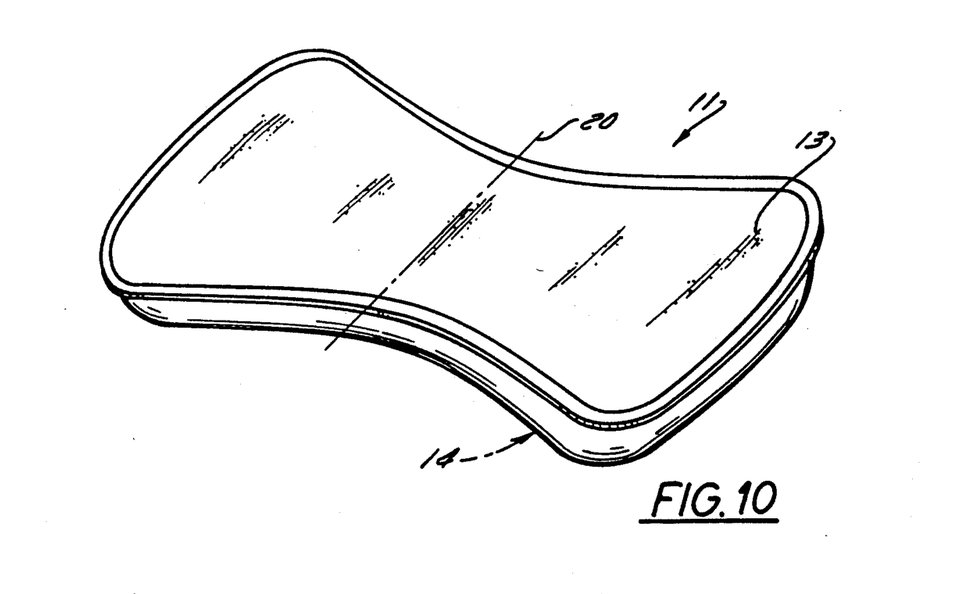

FIG. 10 is another sanitary pad style having a porous sheet 13 on one face and a fluid impermeable backing sheet 14 on the bottom side. This larger and thicker pad is usually folded only on one line such as the one marked 20.

Figure 1:
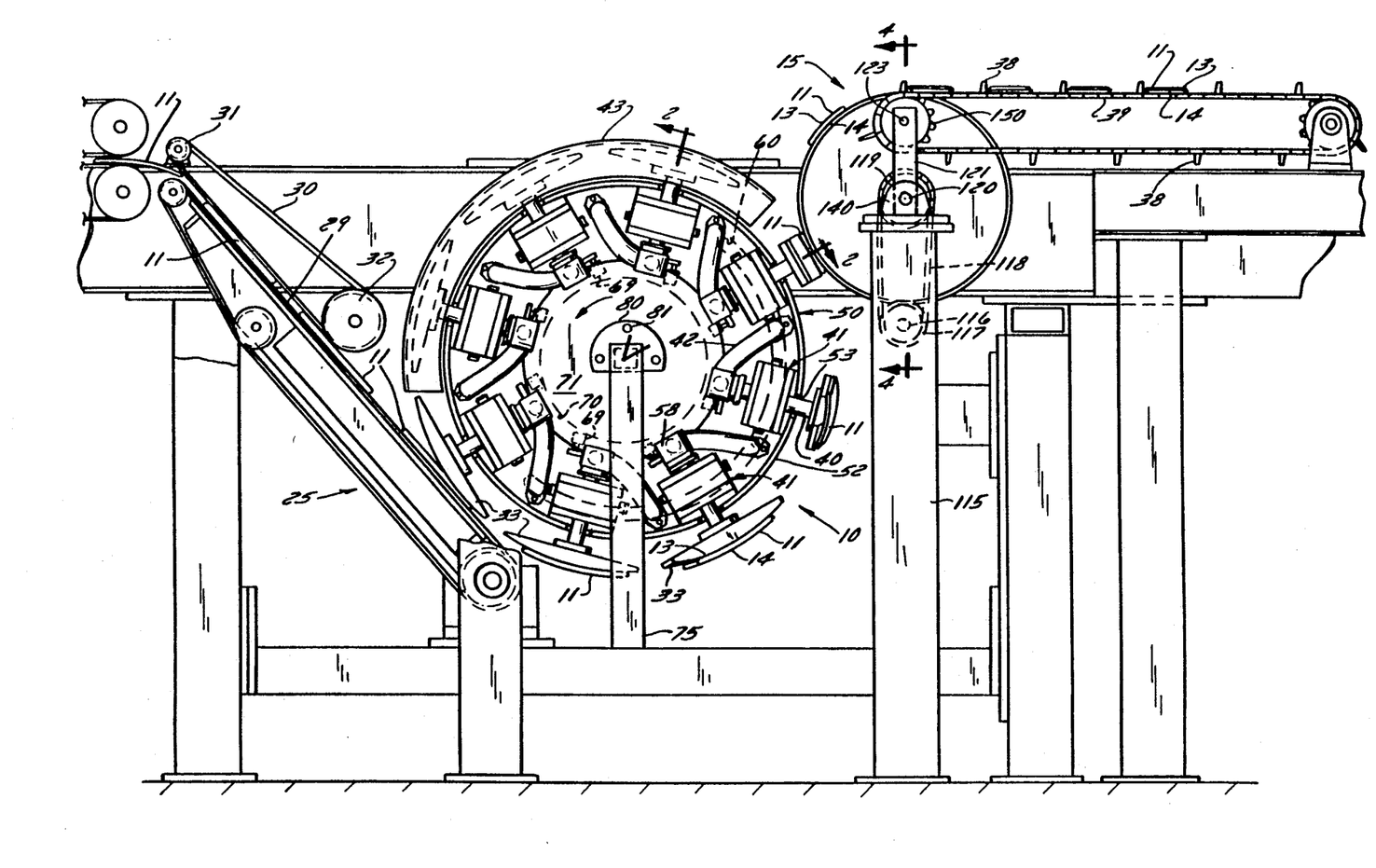
FIG. 1 is a front elevational view of the new pad turning device in conjunction with a pad infeed conveyor and a vacuum drum for removing the turned pads from successive shoes on the rotor.

Attention is now invited to FIG. 1 wherein the pad turning device is again designated generally by the numeral 10. Pads 11 are fed to the turning device by means of a known type of conveyor 25. Pads 11 are retained on belt 29 by a closed loop belt 30 which runs on pulleys 31 and 32 The pads 11 are advanced along belt 29 to the pad pickup station wherein they are put in interfacing relation with the first in a group of orbiting vacuum shoes such as the one marked 33. The pad turner 10 on which the vacuum shoes 33 are carried is assumed to be rotating counterclockwise as viewed in FIG. 1. The successive pads being fed into the pad turner for being turned 90° are carried around on the shoes 33 until reaching a vacuum drum 15 at a release station which drum attracts the pad from the shoe that is in proximity with the vacuum drum at a time when the vacuum which is applied by the shoe is relieved. In accordance with the invention, after the vacuum shoe which has just picked up a pad from the conveyer belt 29 orbits away from the belt, the shoe begins to rotate about a radial axis so that finally, by the time the shoe reaches the vacuum drum 15, it has turned the pad 90° about an axis which is perpendicular to the plane of the pad. It is the porous faces 13 of the pads that interface with the shoes. The non-porous backing sheet 14 of the pads is then faced outwardly or away from the shoe that carries it. Thus, when the pad transfers from the shoe to the periphery of the vacuum drum 15, the nonporous back sheet 14 of the pad interfaces with the drum and the porous front sheet 13 is presented upwardly and away from the vacuum drum. The pads are picked off of the vacuum drum 15 by the lugs 38 on a closed loop conveyor chain 39 as will be discussed in more detail later.

Vacuum drum 15 and its affiliated parts will be described in detail later. Meanwhile the new rotary pad turner will be described in more detail. One may see in FIG. 1 that each vacuum shoe 33 is supported on a radially extending axially bored shaft 40. Each shaft 40 extends from a mechanism support member in the form of a housing 41 which contains the mechanism for turning the shoes 90° as they orbit from the pad pickup station on infeed conveyor belt 29 to the pad transfer station where the shoes become contiguous to the vacuum drum 15. As is evident in FIG. 1, there are short lengths of flexible vacuum conducting tubing 42 leading to each one of the actuating mechanism housings 41 for creating suction in the hollow shaft 40 and in each vacuum shoe 33. After the pads are transferred from shoes 33 to the vacuum drum 15, the shoes 33 are quickly turned again through an angle of 90° so they are traveling lengthwise again as they continue their orbiting motion toward the pickup station. The upper part of the orbital path of the vacuum pickup shoes 33 is covered by a guard 43 in FIG. 1.

Figures 2, 3:
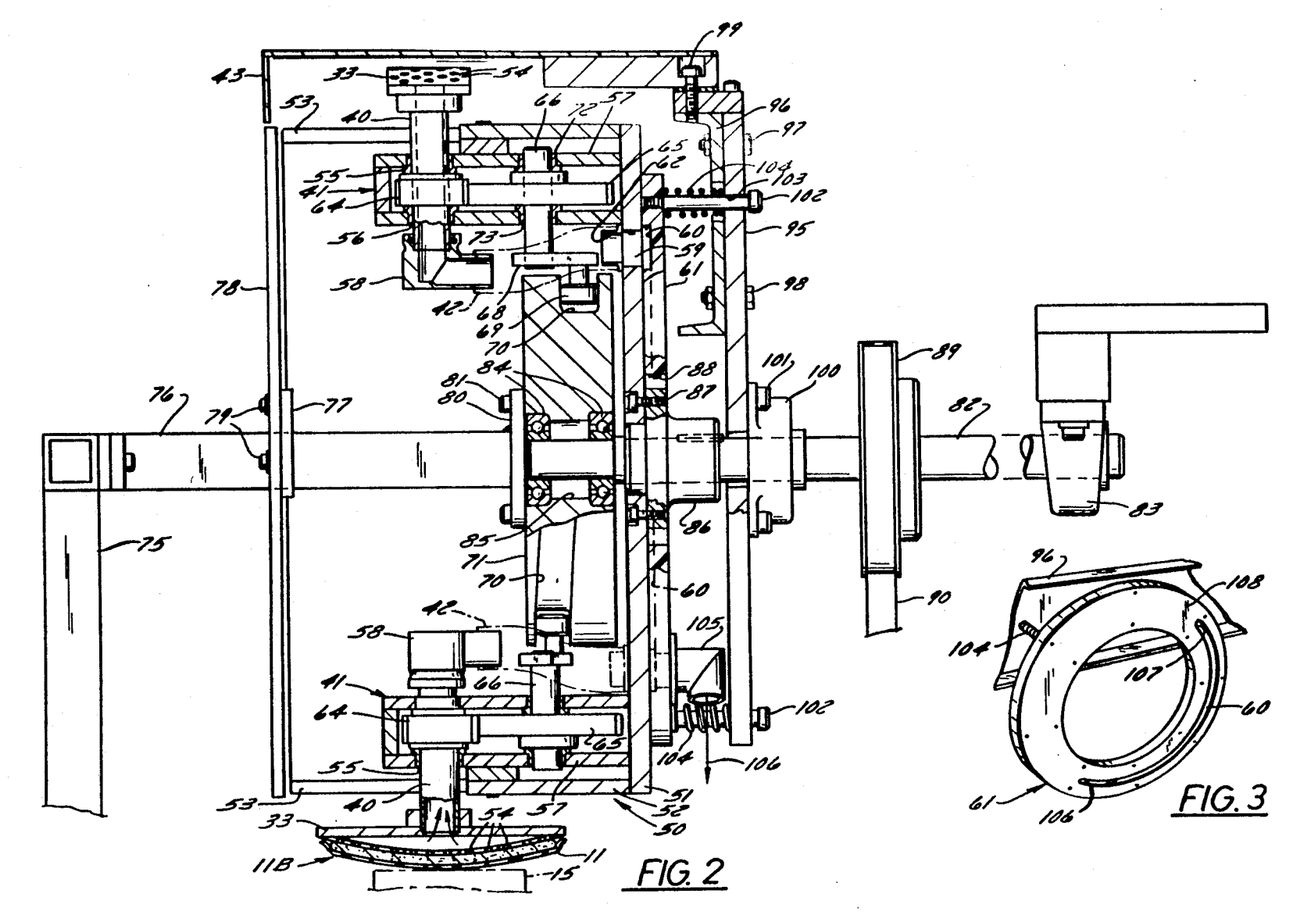
FIG. 2 is a vertical section taken on a line corresponding with 2—2 in FIG. 1.
FIG. 3 is an isolated view or a vacuum platen which is used in the pad turning device depicted in FIG. 2.

Attention is now invited to FIG. 2 for a further description of the pad turning device. The device comprises a rotor constituted by a drum which is generally designated by the numeral 50 and is comprised of a base or end plate 51 and an axially extending wall 52 which has a plurality of axially extending circumferentially spaced apart slots 53 through which the hollow vacuum conducting shafts 40 which carry the vacuum shoes 33 extend. As can be seen near the bottom of FIG. 2 where a pad 11B is about to be transferred from shoe 33 to vacuum drum 15, the curved face of the shoe is provided with a plurality of holes 54 which provide for the pad being drawn against the face of the shoe by vacuum applied through hollow shafts 40. The upper part of FIG. 2 shows especially clearly how axially shafts 40 are journaled in bushings 55 and 56 which are mounted in support members which form housing 41. The support members or housing 41 members are fastened to base plate 51 of the drum and to the axially extending side walls 52 thereof. Typical axially bored vacuum conducting shaft 40 in the upper part of FIG. 2 has a swivel joint 58 connected to it. The base plate 51 of the drum has a vacuum port 59 associated with each one of the shaft turning mechanisms for allowing the swivel coupling 58 to be coupled to a vacuum channel 60 in a vacuum platen 61 which will be described in detail shortly hereinafter. The vacuum port 59 has a nipple 62 extending from it to provide for making a connection by means of the previously mentioned flexible tube 42, shown in phantom lines, to swivel joint 58. The vacuum, of course, is propagated through bored shaft 40 to the holes 54 in the face of the pickup vacuum shoe 33.

For the purpose of turning the shoes back and forth through an angle of 90°, a pinion gear 64 is fastened onto hollow shaft 40. Pinion gear 64 is meshed with a drive gear 65. The drive gear is fastened to a shaft 66 which is journaled in two bushings 72 and 73 which are fixed in drive mechanism support housing 57. A cam follower crank arm 68 is fastened to the shaft 66 and a cam follower roller 69 is mounted to the arm. The cam follower roller of 5 each of the shoe turning mechanisms resides in the groove 70 of a stationary cam 71. When the drum, comprised of base or end plate 51 and side wall 52 rotate, the cam follower arms are caused to swing back and forth through a 45° angle by reason of the cam followers 69 being compelled to follow along a serpentine cam groove 70 in the cam 71. The timing obtained with this cam has already been explained during the discussion of FIG. 1 where it was explained that the vacuum shoes 33 are moving lengthwise at the time an oblong pad 11 is picked up from the infeed conveyor and a complete 90° turn of the shoe is achieved by the time the shoe reaches the transfer station adjacent the vacuum drum 15 where the pad on the shoe is transferred to the vacuum drum.

In FIG. 2 a vertical part 75 of the machine frame has a bracket 76 bolted to it. A bracket plate 77 is fastened to bracket 76 to provide for mounting a stationary closure plate 78 adjacent the open end of rotating drum 50. Plate 78 is mounted by means of machine screws 79. There is another angle bracket 80 forming part of bracket 76. Bracket 80 has the stationary cam 71 mounted to it by means of machine screws 81.

In FIG. 2 the drive shaft for turning the drum 50 for orbiting and turning the vacuum shoes 33 is designated generally by the reference numeral 82. The outboard end of the shaft 82 is journaled in a pillow block 83. The opposite end of the shaft is journaled in a pair of ball bearings 84 whose outer races are fixed in a bore 85 in the center of stationary cam 71. A collar 86 is keyed onto shaft 82. Several screws, such as the one marked 87 pass through base plate 51 of the drum and are threaded into holes in the flange of the collar 86 so that when the shaft 82 is driven rotationally, the collar rotates and thereby causes the base plate 51 and everything carried on it to rotate about the axis of shaft 82. There is a clearance hole 88 in the vacuum platen 61 so the collar can rotate without affecting the vacuum platen. A pulley 89 is fastened to shaft 82 and a belt 90 running on the pulley constitutes the power input to the pad turning device.

FIGS. 2 and 3 show how vacuum is conducted to the internal chambers of curved face shoes 33. A mounting plate 95 is mounted to a fixed channel member 96 of the machine frame by way of a plurality of machine screws such as the ones marked 97 and 98. The guard 43 is also mounted to channel 96 by way of machine screws such as the one marked 99. Mounting plate 95 carries a bearing block 100 which is joined to the mounting plate by means of screws 101. A plurality of screws 102 are free to slide through clearance holes 103 in mounting plate 95. Separate ends of screws 102 are turned into corresponding threaded holes in vacuum platen 61. A coil spring 104 surrounds each machine screw 102 and is interposed between mounting plate 95 and vacuum platen 61. As a result of this construction, the vacuum platen is pressed by the springs into essentially leak proof interfacing relationship with the smooth side of base plate 51 which contains the vacuum ports 59 that are affiliated with each shoe turning mechanism.

FIG. 3 shows the face of vacuum platen 61. As previously mentioned in reference to FIG. 2, the vacuum platen has a vacuum duct or groove 60 formed in it. Although it cannot be seen in FIG. 3, it can be seen in FIG. 2 that there is an elbow 105 that connects to the back side of the vacuum platen for creating a vacuum in groove 60. Vacuum is drawn in the direction of arrow 106 from a vacuum source, not shown, to which elbow 105 is connected. Elbow 105 is connected to the back of vacuum platen 61 in FIG. 3 in alignment with the lower end 106 of groove 60 so the entire length of the groove is always under vacuum. When the rotor 50 is at a rotational angle wherein a pad 11 should be picked up by a vacuum shoe from the infeed conveyor, the vacuum port 59 in the base plate 51 associated with that particular shoe should line up with the lower end 106 in the vacuum groove to thereby initiate application of vacuum to the shoe. Vacuum is maintained as long as the port 59 follows along groove 60 during which time the shoe is turned by the cam and gears through 90° to change the orientation of the pad relative to its line of movement When a particular shoe carrying a pad is in the appropriate position for giving up the pad which it is carrying to the vacuum drum 15, the vacuum port 59 in the base plate 51 will have rotated beyond the end 107 of the vacuum groove 60 and onto the planar surface 108 which results in vacuum being cut off of the shoe so the pad can be yielded to the vacuum drum 15.

Figure 6:
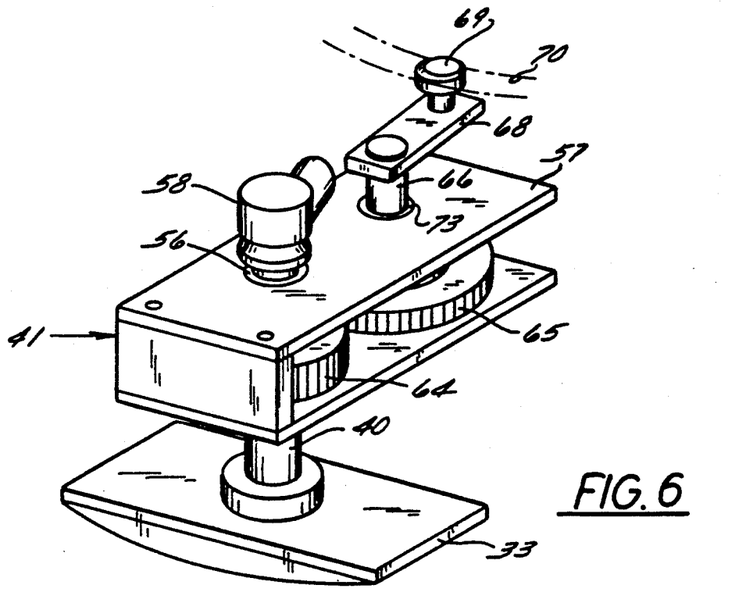
FIG. 6 shows one of the shoes and its associated shoe turning mechanism isolated from the rotor of the pad turning machine showing the shoe which carries a pad as it is oriented before it is turned 90°.

FIG. 6 shows the condition of a typical mechanism for rotating a vacuum shoe 33 at a time when the vacuum port 59 for the particular shoe has run onto the ungrooved flatpart 108 of the vacuum platen 61 and the shoe 33 is on its way to the pickup station where it meets a pad 11 on the infeed conveyor. At this time, the cam follower 69 is running in a straight portion of the cam groove 70 so the cam follower crank arm 63 does not swing nor does the pinion 64 turn so that shoe 33 continues to orbit along a line coincident with its long axis.

Figure 7:
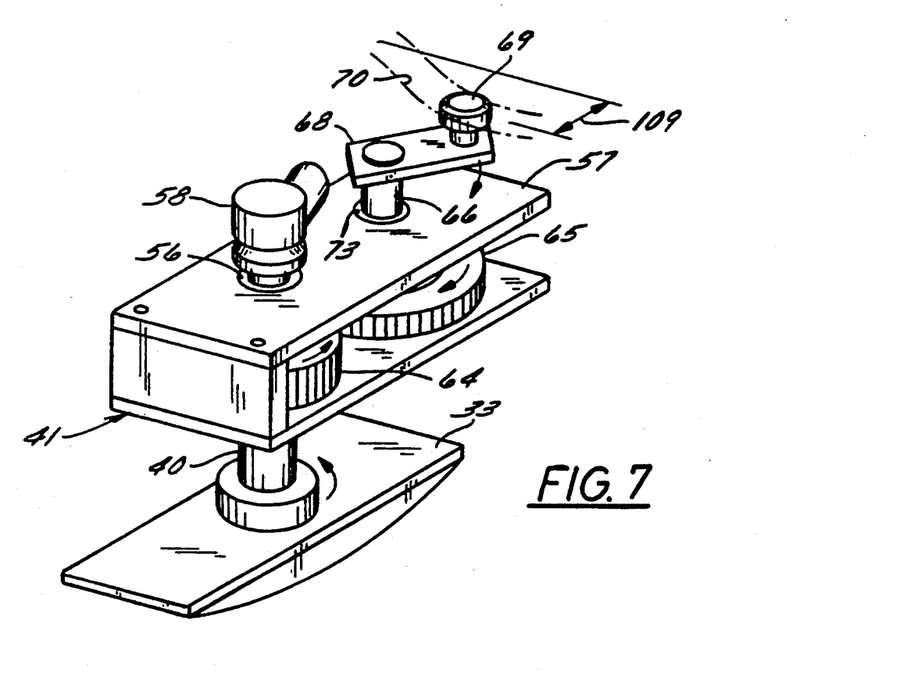
FIG. 7 shows the mechanism of FIG. 6 after it has rotated a pad 90°.

FIG. 7 illustrates the condition of the shoe turning mechanism after the cam follower 69 has run into that part of the cam groove 70 which is offset toward the rotational axis of the cam follower shaft 67 by an amount indicated by the arrow headed line marked 109. The result of this is to swing the cam follower crank arm 63 sufficiently to impart a 90° turn to the shoe 33. This substantial turning angle imparted to the shoe 33 is possible, even though the offset 109 is relatively small, by reason of the ratio of the drive gear 65 to the pinion 64. By way of example and not limitation, the ratio of the gear 65 to the pinion 64 in an actual embodiment is 2:1.

Figures 4, 5:
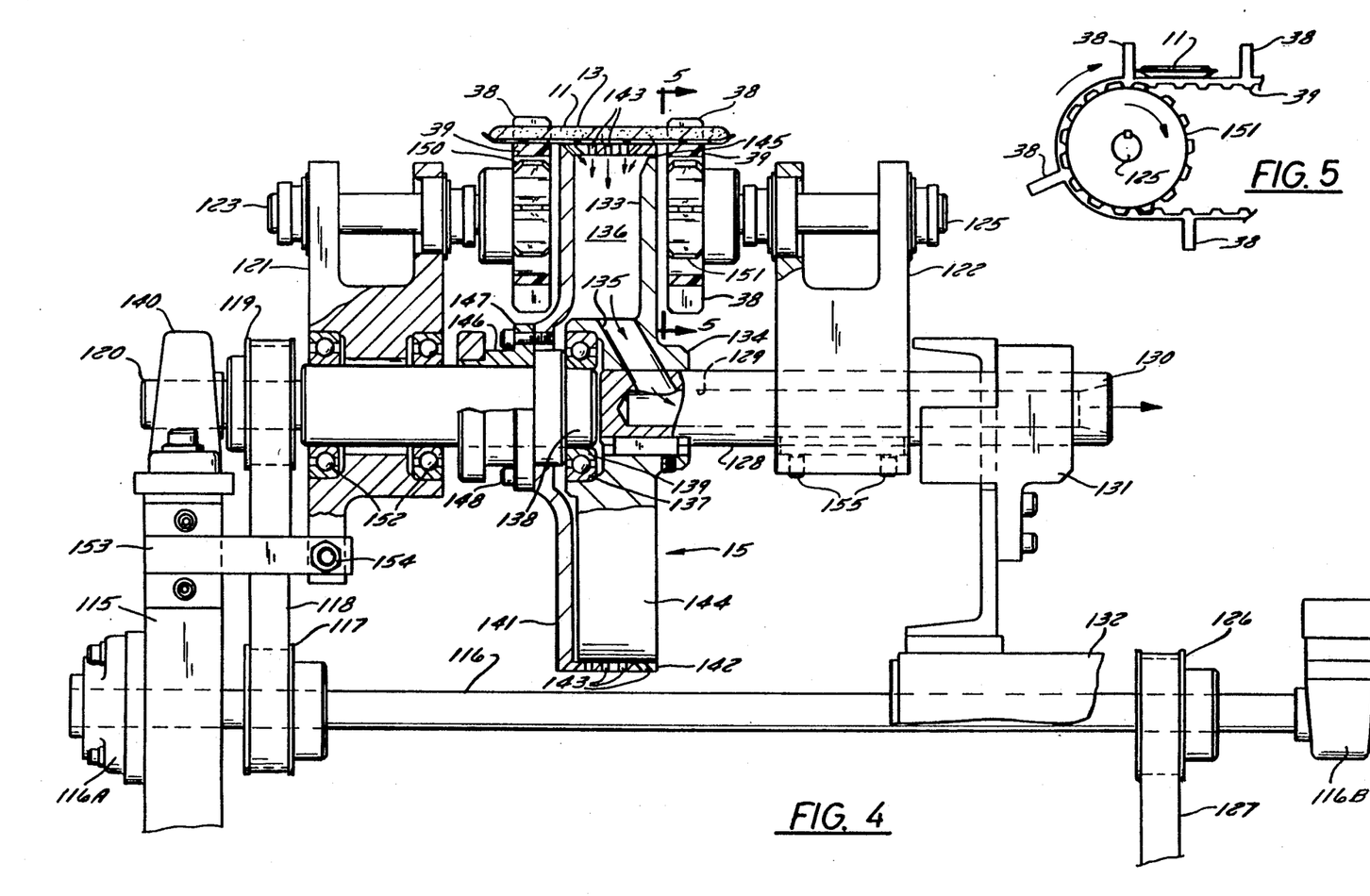
FIG. 4 is a side elevational view of a rotating drum to which the oblong pads are transferred after they have been turned 90° so they are then moving in the direction of their narrow dimension or shorter axis.
FIG. 5 is a view of a part of the transfer station output conveyor taken on a line corresponding with 5—5 in FIG. 4.

A brief discussion of the vacuum drum 15 at the transfer station and its associated conveyor belt 39 will now be undertaken. Refer first to FIG. 1. This figure shows a part of the machine frame 115 to which a shaft 116 is mounted for rotation in bearings. These bearings 116A and 116B are visible in FIG. 4. The power input to the shaft 116 is omitted in FIG. 1. As shown in FIG. 4, the shaft has a pulley 117 fastened to it and the pulley drives a belt 118 which in turn drives another pulley 119 on the shaft 120 on which the vacuum drum 15 is supported for rotation therewith. There are stationarily mounted brackets 121 and 122, only the former being visible in FIG. 1. Bracket 121 has a shaft 123 journaled in it and the other bracket 122 has a shaft 125 journaled in it as shown in FIG. 4. Sprockets 150 and 151 are fastened to shafts 123 and 125, respectively. These are idler sprockets for the closed loop conveyor 39. The dogs 38 on the conveyor belt pick the pads 11 off the vacuum drum 15 and positively push the pads 11 to the right in FIG. 1 where they are taken off at the end of the conveyor at which the conveyor drive pulley 127 is located. After leaving conveyor belt 39, the pads are usually delivered to a folding machine and after that to a packaging machine, neither of the machines being shown.

As shown in FIG. 4, there is a pulley 126 fastened to shaft 116. This pulley is driven by a belt 127 which is the power input to the vacuum drum 15. Located above shaft 116 is a stationary cylindrical rod 128 which contains an axial bore 129. The right end 130 of rod 128 is adapted for being coupled to a vacuum source, not shown. The rod 128 is supported fixedly in a bracket 131 which is mounted to part of the machine frame 132. The vacuum drum 15 is comprised of two parts, a stationary disk 133 and a rotating cup-like part 141. Disk 133 is fastened to stationary rod 128. The disk has an integral central hub 134 in which there is an angulated vacuum duct 135 through which vacuum is communicated from the bore 129 in rod 128 to the space 136 which is contiguous with stationary disk 133.

The outer race 137 of a ball bearing is fixed in stationary hub 134. One end 138 of a rotationally driven shaft 120 fits into the inner race 139 of the ball bearing. The other end of shaft 120 is journaled in a pillow block 140 which is on a post 115 constituting part of the machine frame. As indicated in FIG. 1, and as is true in FIG. 4, shaft 120 has a pulley 119 on it which is driven on a belt 118 which engages with a pulley 117 that is fastened to power input shaft 116.

Rotary shaft 120 has the rotatable part 141 of vacuum drum 15 fastened to it. Part 141 has an axially extending periphery 142 which contains a plurality of small suction holes 143. The holes 143 are in groups which arrive in alignment with the pad on the shoe from which the pad is to be taken from the 5 shoe from the vacuum drum 15. A major part 144 of the stationary disk 141 is solid so it does not provide a vacuum space and seals off all of the groups of small vacuum holes 143 except the group that is lined up with the shoe from which a turned pad is to be taken by the vacuum drum.

The rotationally driven part 141 of the vacuum drum, particularly its periphery 142, fits onto the stationary part with a small clearance gap 145 between them so that the air leaking into the vacuum chamber 136 is minimized.

There is a collar 146 keyed onto the rotatable shaft 120. Collar 146 has a flange portion 147 which has holes through which a plurality of machine screws 148 fit. These machine screws are threaded into the rotatable part 141 of the vacuum drum so the part rotates at the angular speed of shaft 120.

As previously mentioned, in FIG. 4 there are idler sprockets 150 and 151 on shafts 123 and 125, respectively. One of the sprockets 151 is depicted in FIG. 5. It is shown engaged with the conveyor 39. This conveyor is made of flexible urethane material and has a plurality of sprocket engaging teeth extending from one side and dogs or lugs 38 extending from the opposite side. As is evident in FIG. 4, the vacuum drum 15 turns between the two laterally spaced apart sprockets 150 and 151 so that when the lugs 38 come around to the top of the sprockets they can pick the pads off of the vacuum drum and continue their journey to the pad folder which was previously mentioned but is not shown.

The bracket 121 in which the shaft 123 for sprocket 150 is journaled contains ball bearings such as the one marked 152 which allows the shaft 120 to rotate in bracket 121. The bracket itself is supported against rotation on a part 153 of the machine frame to which the bracket is bolted by means of bolts 154.

The other bracket 122 for shaft 125 is simply clamped to stationary rod 128 by means of set screws 155 and some other stabilizing means which are not shown in FIG. 4.

In summary, a new pad turner 10 has been described which is distinguished by its high speed operation, being capable of picking up, turning through an angle of 90° and releasing at least 500 pads per minute. The vacuum pickup shoes 33 used are oblong and are adapted for attracting and holding pads which are as long or even slightly longer than the length of the shoes. Moreover, they can handle pads which are substantially shorter than their length. In the latter case the suction holes in shoes 33 which would be left exposed by the short pads are simply covered with self-adhering tape so vacuum leaks are avoided. Thus, the new pad turner can handle the longest and shortest sanitary pads which any manufacturer is likely to consider without requiring any exchange or adjustment of parts.

Although an illustrative embodiment of the new pad turner has been described in detail, such description is intended to be illustrative rather than limiting, for the invention may be variously embodied and is to be limited only by interpretation of the claims which follow.

We claim:

1. A device for turning a series of articles including pads which have lateral and longitudinal axes and are transported along the line of one of the axes to a pad pickup station after which the pads are turned about an axis perpendicular to said axes while moving to a pad transfer station, said device being positioned proximate to the pickup station and comprising:

a rotationally driven power input shaft, a drum member having a generally flat base plate fastened to said driven shaft for rotation therewith and an annular wall fastened to the base plate concentric to the axis of the driven shaft, a plurality of support members arranged interiorly of said drum member in uniform circumferentially spaced apart relationship, a vacuum conducting shaft which has an axial bore and is journaled for rotating on each support member about an axis which extends radially of the drum member, one end of said vacuum conducting shaft extending radially outwardly of the drum member and another end extending radially inwardly of the drum member, a pad pickup vacuum shoe mounted to the end of each axially bored vacuum conducting shaft which extends radially outwardly of the drum member, said shoe having an internal vacuum chamber which is in communication with the bore of the shaft, means for coupling an end of each of said vacuum conducting shafts which extends radially inwardly of said drum member to a vacuum source, a stationary cam supported in the drum, a shaft journaled for rotation on the respective support members and a first gear fixed on said shaft, a second gear fixed on said axially bored vacuum conducting shaft, the first and second gears being meshed, cam follower means on each support member comprising a crank arm extending radially from the shaft on which said first gear is fixed and a cam follower roller mounted on the arm member, said stationary cam having a cam groove encircling the cam and said roller being engaged in the groove, a part of said groove being offset laterally from the remainder of the groove so as to cause the crank arm to swing and turn the gears and the shaft having the vacuum shoe on it in response to the orbiting crank arm member and follower thereon following the cam groove due to rotation of said drum member.

2. The pad turning device according to claim 1 wherein the ratio of the first gear pitch diameter to the second gear pitch diameter is 2:1.

3. A device for turning a series of articles including pads which have lateral and longitudinal axes and are transported along the line of one of the axes to a pad pickup station after which the pads are turned about an axis perpendicular to said axes while moving to a pad transfer station, said device being positioned proximate to the pickup station and comprising:

a rotationally driven power input shaft, a drum member having a generally flat base plate fastened to said driven shaft for rotation therewith and an annular wall fastened to the base plate concentric to the axis of the driven shaft, a plurality of support members arranged interiorly of said drum member in uniform circumferentially spaced apart relationship, a vacuum conducting shaft which has an axial bore and is journaled for rotating on each support member about an axis which extends radially of the drum member, one end of said vacuum conducting shaft extending radially outwardly of the drum member and another end extending radially inwardly of the drum member, a pad pickup vacuum shoe mounted to the end of each axially bored vacuum conducting shaft which extends radially outwardly of the drum member, said shoe having an internal vacuum chamber which is in communication with the bore of the shaft, means for coupling an end of each of said vacuum conducting shafts which extends radially inwardly of said drum member to a vacuum source, cam follower means on each support member and means on said support member coupling said cam follower means in driving relation to the axially bored vacuum conducting shaft for turning the shaft and the shoe mounted thereon through an angle about the axis of the shaft, and a stationary cam with which said follower means are operatively engaged, rotation of said drum member resulting in actuation of said cam follower means and turning of said shoe beginning with the shoe moving away from said pickup station and terminating at least by the time the shoe reaches a pad transfer station, a fixedly mounted support extending into said drum member, said cam being mounted to said support, bearing means in said cam, said rotationally driven power input shaft having one end supported for rotation by said bearing means and a bearing support having a bearing means thereon displaced axially of the bearing means in the cam for additionally supporting said driven power input shaft.

4. A device for turning a series of articles including pads which have lateral and longitudinal axes and are transported along the line of one of the axes to a pad pickup station after which the pads are turned about an axis perpendicular to said axes while moving to a pad transfer station, said device being positioned proximate to the pickup station and comprising:

a rotationally driven power input shaft, a drum member having a generally flat base plate fastened to said driven shaft for rotation therewith and an annular wall fastened to the base plate concentric to the axis of the driven shaft, a plurality of support members arranged interiorly of said drum member in uniform circumferentially spaced apart relationship, a vacuum conducting shaft which has an axial bore and is journaled for rotating on each support member about an axis which extends radially of the drum member, one end of said vacuum conducting shaft extending radially outwardly of the drum member and another end extending radially inwardly of the drum member, a pad pickup vacuum shoe mounted to the end of each axially bored vacuum conducting shaft which extends radially outwardly of the drum member, said shoe having an internal vacuum chamber which is in communication with the bore of the shaft, means for coupling an end of each of said vacuum conducting shafts which extends radially inwardly of said drum member to a vacuum source, cam follower means on each support member and means on said support member coupling said cam follower means in driving relation to the axially bored vacuum conducting shaft for turning the shaft and the shoe mounted thereon through an angle about the axis of the shaft, and a stationary cam with which said follower means are operatively engaged, rotation of said drum member resulting in actuation of said cam follower means and turning of said shoe beginning with the shoe moving away from said pickup station and terminating at least by the time the shoe reaches a pad transfer station, a rotationally driven shaft to which the vacuum drum is concentric, said shaft having an end, a rod fixed against rotation and arranged in alignment with the axis of said rotationally driven shaft and in end-to-end relationship with the rotationally driven shaft, said vacuum drum comprising two major parts, one of which is a rotating circular member fastened to said rotationally driven shaft for rotation therewith and said peripheral wall extending axially of said circular member, the other part of said drum is a stationary circular member fixed on said rod and having an outside diameter slightly for fitting with small clearance into said circular interior of the rotating circular member to define a vacuum chamber in conjunction with said stationary circular member, said stationary circular member having a vacuum port for drawing a vacuum in said chamber, and a bearing arranged centrally of said stationary circular member and interposed between said stationary circular member and said end of the rotationally driven shaft.

5. The apparatus according to claim 4 wherein said rod has a lengthwise extending bore connected with said vacuum port near one end and adapted at the other end for being connected to a vacuum source.

6. A device for turning a series of oblong pads which have major and minor axes and are transported along the line of one of said axes and are turned about an axis perpendicular to said axes after having arrived at a pad pickup station and are in motion toward a pad transfer station, said device comprising:

a cam and means for supporting said cam in a fixed position, said cam having a circular cam groove including an offset portion formed about the axis of the cam, a rotationally driven power input shaft having an end journaled in said cam with the axis of said shaft coincident with the axis of the cam, a drum member having an annular wall and a circular end plate joined coaxially with the wall, the end plate being fastened to said rotationally driven power input shaft for effecting rotation of the drum, a plurality of support members mounted in said drum equiangularly spaced apart around the axis of the driven power input shaft, an axially bored shaft, for drawing a vacuum, journaled for rotation on each support member, the axis of the bored shaft extending radially of the drum, said bored shaft having an end presented outwardly and an opposite end presented inwardly of the drum member, a pinion gear fixedly mounted on the bored shaft coaxially of the shaft, a driving gear having a shaft, journaled for rotation on the support member and meshed with said pinion gear, a crank arm fastened to the shaft of the driving gear and a cam follower on the arm engaged in the groove of the cam such that as the drum member rotates said crank arm swings in one direction and the other as said follower enters and leaves the offset portion of the cam groove, swinging of said crank arm causing said gear to turn said bored shaft, about its axis through a predetermined angle, a vacuum shoe having an internal chamber and a pad pickup surface on the shoe having a plurality of openings for communicating vacuum from the chamber to the surface, said shoe being mounted to the bored shaft with the chamber connected to the bore, a swivel joint connected to the bored shaft at said inwardly presented end, a plurality of ports in said circular end plate of the drum member arranged equiangularly about the axis of the drum member and flexible tubular elements connecting the ports to the respective swivel joints, a stationarily mounted vacuum platen having a planar surface interfaced with said circular end of the drum member, said planar surface containing a curved groove concentric to and partially encircling the rotational axis of the drum member, the groove having a port for communicating with a vacuum source, said ports on said end plate of the drum being positioned such that they pass successively onto the groove when the shoes arrive at the said pickup station to pick up a pad under the influence of suction applied by the shoes and pass off the groove to remove vacuum from the shoes and release the pad from the shoes when said shoes arrive successively at said pad transfer station.

* * * * *

UNITED STATES PATENT AND TRADEMARK OFFICE
CERTIFICATE OF CORRECTION

PATENT NO. : 5,025,910

DATED : June 25, 1991

INVENTOR(S) : Randal D. Lasure, et al

It is certified that error appears in the above-identified patent and that said Letters Patent is hereby corrected as shown below:

Column 10, line 44:
   After "slightly" insert --- smaller than the inside diameter of said rotating circular member ---.

Signed and Sealed this

Seventeenth Day of November, 1992

Attest:

DOUGLAS B. COMER

*Attesting Officer*   Acting Commissioner of Patents and Trademarks